United States Patent [19]  [11] 4,062,835
Tinney  [45] Dec. 13, 1977

[54] PENTAPEPTIDES AND METHODS FOR THEIR PRODUCTION

[75] Inventor: Francis John Tinney, Ann Arbor, Mich.

[73] Assignee: Parke, Davis & Company, Detroit, Mich.

[21] Appl. No.: 699,123

[22] Filed: June 23, 1976

[51] Int. Cl.$^2$ ............................................. C07C 103/52
[52] U.S. Cl. .................... 260/112.5 LH; 260/112.5 R; 424/177
[58] Field of Search .................. 260/112 LH, 112.5 R

[56] References Cited
U.S. PATENT DOCUMENTS 3,796,697   3/1974   Flouret ...................... 260/112.5 LH

OTHER PUBLICATIONS

Biochem. and Biophys. Res. Comm. (1974) 57, 1248–1256.
Biochem. and Biophys. Res. Comm. (1974) 60, 406–412.

Primary Examiner—Delbert R. Phillips
Attorney, Agent, or Firm—Stephen Raines; David B. Ehrlinger; Frank S. Chow

[57] ABSTRACT

New pentapeptides having the formula X-R-Tyr-(methyl)-Ser(benzyl)-R$^1$-Y wherein X is t-butoxycarbonyl or benzyloxycarbonyl, R is a single amino acid fragment, a dipeptide fragment or tripeptide fragment utilizing amino acids selected from the group consisting of Pro, Aze, His-(benzyl) and Trp; R$^1$ is a single bond or a single amino acid fragment or a dipeptide fragment utilizing amino acids selected from the group consisting of Ala, Trp and His and Y is lower alkoxy, amino, lower alkylamino or di(lower alkyl)amino with the proviso that the total number of amino acid units when R and R$^1$ are combined is three.

4 Claims, No Drawings

PENTAPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new N-protected pentapeptides that are represented by the formula

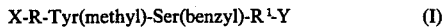

X-R-Tyr(methyl)-Ser(benzyl)-R¹-Y        (I)

wherein X is t-butoxycarbonyl or benzyloxycarbonyl, R is a single amino acid fragment, a dipeptide fragment or tripeptide fragment utilizing amino acids selected from the group consisting of Pro, Aze, His(benzyl) and Trp; R¹ is a single bond or a single amino acid fragment or a dipeptide fragment utilizing amino acids selected from the group consisting of Ala, Trp and His and Y is lower alkoxy, amino, lower alkylamino or di(lower alkyl)amino with the proviso that the total number of amino acid units when R and R¹ are combined is three.

The preferred compounds of formula I are those wherein X is t-butoxycarbonyl, R is His(benzyl), R¹ is Trp Ala and Y is lower alkoxy or lower alkylamino.

In formula I, the conventional symbols for amino acid residues of peptide compounds linked thereto are used and each is intended to have the following meaning: Pro, D-prolyl or L-prolyl; Aze, D-2-azetidinylcarbonyl or L-2-azetidinylcarbonyl; His(benzyl), N^im-benzyl-D-histidyl or N^im-benzyl-L-histidyl; Trp, D-tryptophyl or L-tryptophyl; Ala, D-alanyl or L-alanyl; His, D-histidyl or L-histidyl; Tyr(methyl), D-tyrosyl(methyl) or L-tyrosyl(methyl) and Ser(benzyl), D-seryl(benzyl) or L-seryl(benzyl). In addition, the term "lower alkyl" is intended to mean a straight, branched or cyclic hydrocarbon moiety of up to six carbon atoms, such as methyl, ethyl, isopropyl and cyclopropyl and "lower alkoxy" is intended to mean an alkoxy group having a straight, branched or cyclic hydrocarbon moiety of up to six carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein X, R and R¹ are as previously defined and Y is lower alkoxy, are produced by removing a protected pentapeptide from a resin complex of the following structure

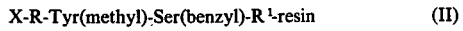

X-R-Tyr(methyl)-Ser(benzyl)-R¹-resin        (II)

wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected pentapeptide through a methyleneoxy bridge wherein the methylene group is attached to the polymeric portion of the resin and the oxygen atom is attached to the protected pentapeptide and X, R and R₁ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° C. to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein Y is amino, lower alkylamino or di(lower alkyl)amino may be prepared by reacting compounds of the formula II wherein X, R and R¹ are as previously defined, with ammonia, lower alkylamine or di(lower alkyl)amine.

The resin complex is suspended in a solvent, such as methanol, ethanol, dimethylformamide, etc., at a temperature of from about 0° C. to 50° C. for periods of from 12 hours to 10 days. When employing less reactive amines, the preferred solvent is dimethylformamide.

The complex resins of the formula II are prepared by coupling a protected amino acid of the formula

X—R—OH        (III)

wherein X is as previously defined and R is Pro, Aze, His(benzyl) or Trp with complex resins of the formula

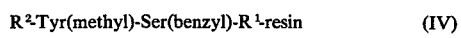

R²-Tyr(methyl)-Ser(benzyl)-R¹-resin        (IV)

wherein R¹ is as previously described and R² is hydrogen, a single amino acid fragment or a dipeptide fragment utilizing the amino acids Pro, Aze, His(benzyl) or Trp with the proviso that the total number of amino acid units when R¹ and R² are combined is two, in an organic solvent, such as dichloromethane with the aid of dicyclohexylcarbodiimide. The three reactants may be used in about equimolar quantities, but excess amounts of the protected amino acid and dicyclohexylcarbodiimide are sometimes advantageous. The reaction is generally conducted at about room temperature for a period of from about 15 minutes to about 20 hours.

The complex resins of the formula IV are prepared by treating complex resins of the formula

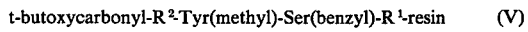

t-butoxycarbonyl-R²-Tyr(methyl)-Ser(benzyl)-R¹-resin        (V)

wherein R¹ and R² are as described in formula IV with the proviso that the total number of amino acid units when R¹ and R² are combined is two with a large excess of trifluoroacetic acid utilizing dichloromethane as the solvent at temperatures of from 20° C. to 30° C. for about 10 minutes followed by neutralization of the trifluoroacetic acid salt with a base such as triethylamine.

Certain of the complex resins of formula V are prepared by coupling

t-butoxycarbonyl-R³-OH wherein R³ is Pro, Aze, His(benzyl) or Trp, to complex resins of the formula

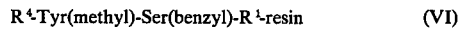

R⁴-Tyr(methyl)-Ser(benzyl)-R¹-resin        (VI)

wherein R¹ is a single bond, Ala, Trp or His, R⁴ is hydrogen, Pro, Aze, His(benzyl) or Trp with the proviso that when $R^1$ is an amino acid $R^4$ is hydrogen and when $R^4$ is an amino acid, $R^1$ is a single bond using the reaction procedure described for the preparation of compounds of the formula II.

The complex resins of the formula VI are prepared by treating the complex resins of the formula $$\text{t-butoxycarbonyl-}R^4\text{-Tyr(methyl)-Ser(benzyl)-}R^1\text{-resin} \quad \text{(VII)}$$

wherein $R^1$ and $R^4$ are as described for formula VI with trifluoroacetic acid using the reaction procedure for the preparation of compounds of the formula IV.

Certain of the complex resins of the formula VII are prepared by coupling $$\text{t-butoxycarbonyl-}R^4\text{-OH}$$

wherein $R^4$ is Pro, Aze, His(benzyl) or Trp to complex resins of the formula $$\text{Tyr(methyl)-Ser(benzyl)-}R^1\text{-resin} \quad \text{(VIII)}$$

wherein $R^1$ is a single bond according to the procedure used for the preparation of compounds of formula II.

The complex resins of the formula VIII are prepared by treating the complex resins of the formula $$\text{t-butoxycarbonyl-Tyr(methyl)-Ser(benzyl)-}R^1\text{-resin} \quad \text{(IX)}$$

wherein $R^1$ is as described in formula VIII with trifluoroacetic acid using the reaction procedure for the preparation of compounds of the formula IV.

The complex resins of the formula IX and other useful complex resins are prepared by coupling $$\text{t-butoxycarbonyl-Tyr(methyl)-OH}$$

to complex resins of the formula $$\text{Ser(benzyl)-}R^1\text{-resin} \quad \text{(X)}$$

wherein $R^1$ is as described in formula I, according to the procedure used for the preparation of compounds of formula II.

The complex resins of the formula X are prepared by treating the complex resins of the formula $$\text{t-butoxycarbonyl-Ser(benzyl)-}R^1\text{-resin} \quad \text{(XI)}$$

wherein $R^1$ is as described in formula I with trifluoroacetic acid using the reaction procedure for the preparation of compounds of the formula IV.

The complex resins of formula XI are prepared by coupling $$\text{t-butoxycarbonyl-Ser(benzyl)-OH}$$

to complex resins of the formula $$R^1\text{-resin} \quad \text{(XII)}$$

wherein $R^5$ is an amino acid or dipeptide utilizing amino acids selected from the group consisting of Ala, Trp and His, according to the procedure used for the preparation of compounds of formula II.

The complex resins of the formula XII are prepared by treating the complex resins of the formula $$\text{t-butoxycarbonyl-}R^5\text{-resin} \quad \text{(XIII)}$$

wherein $R^5$ is as described in formula XII, with trifluoroacetic acid using the reaction procedure for the preparation of compounds of formula IV.

Certain of the complex resins of the formula XIII are prepared by coupling $$\text{t-butoxycarbonyl-}R^6\text{-OH} \quad \text{(XIV)}$$

wherein $R^6$ is Ala, Trp or His to complex resins of the formula $$R^7\text{-resin} \quad \text{(XV)}$$

wherein $R^7$ is Ser(benzyl), Ala, Trp or His, according to the procedure used for the preparation of compounds of formula II.

The complex resins of the formula XV are prepared by treating the complex resins of the formula $$\text{t-butoxycarbonyl-}R^7\text{-resin} \quad \text{(XVI)}$$

wherein $R^7$ is as described for formula XV, with trifluoroacetic acid using the reaction procedure for the preparation of compounds of formula IV.

In accordance with this invention, compounds of the formula I, wherein X, R and $R^1$ are as previously described and Y is amino, lower alkylamino or di(lower alkyl)amino are prepared by reacting a compound of the formula I wherein Y is alkoxy, preferably methoxy, with ammonia, lower alkylamine or di(lower alkylamine).

The reactions are conducted at temperatures of from about 5° C. to 100° C. for from three hours to four days, preferably about room temperature. Generally, a large excess of amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein X, R and $R^1$ are as previously defined and Y is amino, lower alkylamino or di(lower alkyl)amino are prepared by reacting a compound of the formula $$\text{X-R-Tyr(methyl)-Ser(benzyl)-}R^1\text{-N}_3 \quad \text{(XVII)}$$

with ammonia, lower alkylamine or di(lower alkyl)amine in a non-reactive solvent such as dimethylformamide, dioxane, tetrahydrofuran or mixtures thereof. The reaction is carried out at about −30° C. to about 0° C. for about 12 to 24 hours, preferably −20° C. to 0° C. for from 16 to 19 hours. The two reactants are used in approximately equimolar amounts although a slight excess of the amine, about 10 percent, is preferred. When X is t-butoxycarbonyl, care should be taken to avoid the presence of a large excess of acid.

The azide compounds of the formula XVII are normally prepared in situ by reacting a peptide hydrazide of the formula $$\text{X-R-Tyr(methyl)-Ser(benzyl)-}R^1\text{-NHNH}_2 \quad \text{(XVIII)}$$

wherein X, R and $R^1$ are as defined in formula I with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −30° C. and 0° C. following the in situ formation of the azide of formula XVII and prior to the further reaction of the peptide azide with the appropriate amine to form certain pentapeptides of formula I, a tertiary amine such as triethylamine is added to the reaction mixture to neutralize the acid used.

The compounds of formula XVIII are prepared by reacting a compound of formula I wherein Y is methoxy with hydrazine hydrate in methanol.

Compounds of the formula I wherein X, R and $R^1$ are as described in formula I and Y is amino, lower alkylamino or di(lower alkyl)amino are prepared by coupling a compound of the formula

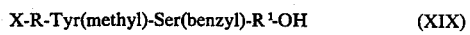

$$X\text{-}R\text{-}Tyr(methyl)\text{-}Ser(benzyl)\text{-}R^1\text{-}OH \qquad (XIX)$$

with ammonia, a lower alkylamine or a di(lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° C. to 50° C., preferably room temperature for periods of from 10 hours to 5 days.

1-Hydroxybenzotriazole may be used in the above reaction in addition to the dicyclohexylcarbodiimide. The 1-hydroxybenzotriazole is added in a ratio of one to two equivalents when compared to the reactants.

The compounds of the formula XIX are prepared by the hydrolysis of a compound of formula I wherein X, R and $R^1$ are as previously defined and Y is lower alkoxy. The reaction is conducted at temperatures of from 20° C. to 30° C. using about 0.5 ml. of two normal aqueous sodium hydroxide solution and 10 ml. of solvent, usually water or an alcohol such as methanol, for each millimole of ester. The compound of formula XIX is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Pentapeptides of this invention were screened for LRF antagonist activity in vitro using rat anterior pituitary cell cultures as described by Vale et. al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on certain preferred compounds.

| ACTIVITY TABLE FOR IN VITRO TEST IN RAT ANTERIOR PITUITARY CELL CULTURES | | | |
|---|---|---|---|
| | Molar Conc. | LH Value ng/ml. | % LH Release Inhibition |
| $N^\alpha$-t-butoxycarbonyl-$N^{im}$-benzyl-L-histidyl-O-methyl-L-tyrosyl-O-benzyl-L-seryl-L-tryptophyl-D-Alanine-N-ethyl amide | $6 \times 10^{-7}$ | 7.72 | 98 |
| | $3 \times 10^{-7}$ | 10.16 | 90 |
| | $1 \times 10^{-7}$ | 17.2 | 69 |
| | $5 \times 10^{-8}$ | 21.61 | 56 |
| LRF Control | $3.5 \times 10^{-10}$ | 40.46 | |
| Saline Control | | 6.46 | |
| $N^\alpha$-t-butoxycarbonyl-$N^{im}$-benzyl-L-histidyl-O-methyl-L-tyrosyl-O-benzyl-L-seryl-L-tryptophyl-D-alanine methyl ester | $1 \times 10^{-6}$ | 16.89 | 69 |
| LRF Control | $2.5 \times 10^{-10}$ | 36.96 | |
| Saline Control | | 7.70 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511–512. Thus, the pentapeptides of this invention are useful in controlling ovulation and in restricting fertility.

The invention is illustrated by the following examples.

EXAMPLE 1

$N^\alpha$-t-Butoxycarbonyl-$N^{im}$-benzyl-L-histidyl-O-methyl-L-tyrosyl-O-benzyl-L-seryl-L-tryptophyl-D-alanine methyl ester $N^\alpha$-t-Butoxycarbonyl-$N^{im}$-benzyl-L-histidyl-O-methyl-L-tyrosyl-O-benzyl-L-seryl-L-tryptophyl-D-alanine resin, 4 g., is stirred with 50 ml. of triethylamine in 500 ml. of methanol at room temperature for 2 days. The resin is separated and the solution evaporated. The residue is chromatographed on silica gel with 10% methanol in benzene; 1.0 g.; m.p. 85°–90° C.

General Procedure for the Solid Phase Synthesis of Peptide Resins

The peptide resin is obtained by attaching an α-amino protected amino acid to a resin (usually a chloromethylated resin which is commerically available from Lab Systems, Inc., San Mateo, Calif.). The peptide system is then constructed by de-protecting the α-amino-protected amino acid resin and attaching an α-amino-protected amino acid. Repetition of this process produces the peptide resin having the required number and sequence of the desired peptide. The terminal α-amino protection is changed by de-protection and attaching the desired carboxylic terminal group. The solid phase synthesis procedure is described by J. M. Stewart "Solid Phase Peptide Synthesis," W. H. Freeman and Co., 1969.

Each cycle of the procedure follows the scheme:
1. De-protection with excess 50% trifluoroacetic acid in dichloromethane.
2. Three washes with dichloromethane.
3. Neutralization of the trifluoroacetic acid salt with an excess of cold 10% triethylamine in dichloromethane.
4. Three washes with dichloromethane.
5. Fifteen to 30 minutes agitation with the α-amino-protected amino acid in 20% molar excess (based on the resin nitrogen analysis). In an alternate method, a 4-fold excess of the α-amino-protected amino acid is agitated with the resin for 15 minutes and the excess recovered by draining the solution from the reactor.
6. Addition of dicyclohexylcarbodiimide at least equivalent to the α-amino-protected amino acid in Step 5 in dichloromethane followed by agitation for 4 to 20 hours. In the alternate method, a 3.3-fold excess of dicyclohexylcarbodiimide is used relative to the α-amino-protected amino acid resin.
7. Three washes with dichloromethane.

$N^\alpha$-t-Butoxycarbonyl-$N^{im}$-benzyl-L-histidyl-O-methyl-L-tyrosyl-O-benzyl-L-seryl-L-tryptophyl-D-alanine resin is obtained from 16.3 g. (0.011 mol) of $N^\alpha$-t-butoxycarbonyl-D-alanine resin by reacting successively, according to the above procedure with (1) 5.3 g. (0.017 mol) of $N^\alpha$-t-butoxycarbonyl-L-tryptophan and 3.3 g. (0.016 mol) of dicyclohexylcarbodiimide, (2) 4.7 g. (0.016 mol) of $N^\alpha$-t-butoxycarbonyl-O-benzyl-L-serine and 3.3 g. of dicyclohexylcarbodiimide, (3) using 7.7 g. of resin of 23 g. from the prior step, 1.6 g. (0.0043 mol) of $N^\alpha$-t-butoxycarbonyl-O-methyl-L-tyrosine and 1.09 g. (0.0053 mol) of dicyclohexylcarbodiimide and (4) using 3.9 g. of resin from 6.9 g. obtained in the prior step, 1 g. (0.003 mol) of $N^\alpha$-t-butoxycarbonyl-$N^{im}$-benzyl-L-histidine and 0.62 g. (0.003 mol) of dicyclohexylcarbodiimide.

$N^\alpha$-t-Butoxycarbonyl-D-alanine resin is obtained by mixing 100 g. of chloromethylated resin crosslinked with 1% divinylbenzene, 35 g. of $N^\alpha$-t-butoxycarbonyl-D-alanine and 18.5 g. of triethylamine in 500 ml. of ethanol at reflux for 3 days, filtered and washed with ethanol, water, methanol and ether. After drying, analysis shows 0.00066 mol of $N^\alpha$-t-butoxycarbonyl-D-alanine/gram.

EXAMPLE 2

$N^\alpha$-t-Butoxycarbonyl-$N^{im}$-benzyl-L-histidyl-O-methyl-L-tyrosyl-O-benzyl-L-seryl-L-tryptophyl-D-alanine N-ethylamide The methyl ester of Example 1, 0.3 g., is dissolved in 200 ml. of methanol and 5 ml. of ethylamine added at room temperature. The mixture is kept in a closed container for 3 days followed by evaporation of the volatile components. The residue is chromatographed on silica gel with ten percent methanol in benzene. The product is isolated after removal of the solvent; 0.22 g.; m.p. 98°–103° C.

EXAMPLE 3

According to the procedure of Example 2, upon substituting in place of ethylamine one of the following amines butylamine,
diethylamine and
dipropylamine, one obtains $N^\alpha$-t-Butoxycarbonyl-$N^{im}$-benzyl-L-histidyl-O-methyl-L-tyrosyl-O-benzyl-L-seryl-L-tryptophyl-D-alanine N-butylamide,
$N^\alpha$-t-Butoxycarbonyl-$N^{im}$-benzyl-L-histidyl-O-methyl-L-tyrosyl-O-benzyl-L-seryl-L-tryptophyl-D-alanine N,N-diethylamide, and
$N^\alpha$-t-Butoxycarbonyl-$N^{im}$-benzyl-L-histidyl-O-methyl L-tyrosyl-O-benzyl-L-seryl-L-tryptophyl-D-alanine N,N-dipropylamide, respectively.

EXAMPLE 4

According to the procedure of Example 1, upon substituting in place of $N^\alpha$-t-Butoxycarbonyl-$N^{im}$-benzyl-L-histidyl-O-methyl-L-tyrosyl-O-benzyl-L-seryl-L-tryptophyl-D-alanine resin, one of the following $N^\alpha$-t-Butoxycarbonyl-$N^{im}$-benzyl-L-histidyl-O-methyl-L-tyrosyl-O-benzyl-L-seryl-L-histidyl-L-alanine resin,
$N^\alpha$-t-Butoxycarbonyl-L-prolyl-L-tryptophyl-O-methyl-L-tyrosyl-O-benzyl-L-seryl-L-alanine resin and $N^\alpha$-t-Butoxycarbonyl-$N^{im}$-benzyl-L-histidyl-D-prolyl-D-tryptophyl-O-methyl-L-tyrosyl-O-benzyl-L-serine resin one obtains $N^\alpha$-t-Butoxycarbonyl-$N^{im}$-benzyl-L-histidyl-O-methyl-L-tyrosyl-O-benzyl-L-seryl-L-histidyl-L-alanine methyl ester,
$N^\alpha$-t-Butoxycarbonyl-L-prolyl-L-tryptophyl-O-methyl-L-tyrosyl-O-benzyl-L-seryl-L-alanine methyl ester;

and $N^\alpha$-t-Butoxycarbonyl-$N^{im}$-benzyl-L-histidyl-D-prolyl-D-tryptophyl-O-methyl-L-tyrosyl-O-benzyl-L-serine methyl ester, respectively.

I claim:
1. A pentapeptide of the formula

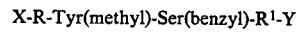

wherein X is t-butoxycarbonyl or benzyloxycarbonyl, R is a single amino acid fragment, a dipeptide fragment or tripeptide fragment utilizing amino acids selected from the group consisting of Pro, Aze, His(benzyl) and Trp; $R^1$ is a single bond or a single amino acid fragment or a dipeptide fragment utilizing amino acids selected from the group consisting of Ala, Trp and His and Y is lower alkoxy, amino, lower alkylamino or di(lower alkyl)amino with the proviso that the total number of amino acid units when R and R¹ are combined is three.

2. The pentapeptides of claim 1 wherein X is t-butoxycarbonyl, R is His(benzyl), R¹ is Trp-Ala and Y is lower alkoxy or lower alkylamino.

3. The pentapeptide of claim 1 having the name N$^\alpha$-t-Butoxycarbonyl-N$^{im}$-benzyl-L-histidyl-O-methyl-L-tyrosyl-O-benzyl-L-seryl-L-tryptophyl-D-alanine methyl ester.

4. The pentapeptide of claim 1 having the name N$^\alpha$-t-Butoxycarbonyl-N$^{im}$-benzyl-L-histidyl-O-methyl-L-tyrosyl-O-benzyl-L-seryl-L-tryptophyl-D-alanine N-ethylamide.

* * * * *